(12) United States Patent
Fröhlich

(10) Patent No.: US 6,719,683 B2
(45) Date of Patent: Apr. 13, 2004

(54) RADIOTHERAPY TREATMENT PLANNING WITH MULTIPLE INVERSE PLANNING RESULTS

(75) Inventor: Stephan Fröhlich, Aschheim (DE)

(73) Assignee: BrainLAB AG, Kirchheim/Heimsteten (DE)

(*) Notice: Subject to any disclaimer, the term of this patent is extended or adjusted under 35 U.S.C. 154(b) by 0 days.

(21) Appl. No.: 09/969,548

(22) Filed: Oct. 1, 2001

(65) Prior Publication Data

US 2002/0080915 A1 Jun. 27, 2002

Related U.S. Application Data

(60) Provisional application No. 60/237,767, filed on Sep. 30, 2000.

(51) Int. Cl.[7] ................................................. A61N 5/00
(52) U.S. Cl. ........................................................ 600/1
(58) Field of Search .............................. 600/1–8, 411, 600/427, 300; 705/3; 378/65

(56) References Cited

U.S. PATENT DOCUMENTS

| 5,373,844 | A | * | 12/1994 | Smith et al. ............... 600/427 |
| 5,458,125 | A | * | 10/1995 | Schweikard ............... 600/407 |
| 6,301,329 | B1 | * | 10/2001 | Surridge .................... 378/65 |
| 6,327,490 | B1 | * | 12/2001 | Spetz ........................ 600/427 |
| 6,385,286 | B1 | * | 5/2002 | Fitchard et al. ............ 378/65 |

* cited by examiner

Primary Examiner—Samuel G. Gilbert
(74) Attorney, Agent, or Firm—Renner, Otto, Boisselle & Sklar, LLP

(57) ABSTRACT

An inverse planning method and apparatus for radiotherapy treatment of a target volume in a body are characterized by using a computer to calculate the results (dose distribution) of multiple treatment solutions (proposed radiation beam arrangements); and simultaneously displaying the calculated results for at least two of the treatment solutions for comparison by a treatment planner to enable the treatment planner to select a desired one of the treatment solutions.

8 Claims, 3 Drawing Sheets

RADIOTHERAPY TREATMENT PLANNING WITH MULTIPLE INVERSE PLANNING RESULTS

RELATED APPLICATION DATA

This application claims priority of U.S. Provisional Application No. 60/237,767 filed Sep. 30, 2000 which is hereby incorporated herein by reference in its entirety.

FIELD OF THE INVENTION

The invention herein described relates to radiotherapy and more particularly to an apparatus and method for treatment planning for radiotherapeutical procedures.

BACKGROUND OF THE INVENTION

Conformal radiation therapy typically employs a linear accelerator as the source of a radiation beam or beams used to treat a tumor and/or other internal anomaly, herein referred to generally as a target volume. The linear accelerator has a radiation beam source which may be rotated about the patient to direct the radiation beam toward the target volume from different angles. Various means have been employed to control the rotation, intensity, shape and/or direction of the radiation beam in accordance with a predetermined treatment program designed to apply a desired radiation dose to the target area while minimizing the dose of radiation to surrounding healthy tissue and/or adjacent healthy organs, hereinafter referred to generally as a non-target volume. Overall, the goal of conformal radiation therapy is to confine the delivered radiation dose to only the treatment volume while minimizing the dose of radiation to the non-target volume. Accordingly, a treatment plan (also referred to as treatment solution) is desired that optimizes the radiation dose to the target area while minimizing the amount of radiation delivered to the surrounding non-target volume.

Existing techniques to optimize treatment planning during radiation oncology include forward treatment planning and the more recent inverse treatment planning. The forward treatment problem is to compute the dose distribution in a tissue given a treatment plan. The inverse treatment problem is to find a treatment plan whose execution will achieve a desired dose distribution.

More particularly, forward treatment planning typically involves loading patient scan data in a computer. Usually a three-dimensional (3D) data set of the patient is used, such as that obtained by CT, MRI or other imaging techniques. The treatment planner then virtually places therapeutic radiation beams within the scan data, adjusting the shape, size, direction and/or intensity of the radiation beam or beams. Next the planning system calculates the resulting dose distribution. If the treatment planner is not satisfied with the results, he/she changes one or more of the beam parameters and starts the calculation again. In an iterative process the treatment planner tries to achieve the desired dose distribution. This can be a tedious and time consuming task.

Inverse treatment planning directly defines the desired dose distribution instead of defining beam parameters. The desired dose distribution may be defined in different ways, e.g., by drawing on the two-dimensional (2D) CT slices. Typically the desired dose distribution is specified by marking forbidden areas (constraints) on a Dose Volume Histogram (DVH) sketch. The DVH is a standard radiotherapy treatment verification tool. Based on the desired dose distribution regardless of how represented, a computer calculates the ideal beam parameters using known optimization techniques. Inverse planning systems are typically used in conjunction with Intensity Modulated RadioTherapy (IMRT) treatments.

Ideally the treatment planner would like to set the constraints in a way that the target volume (e.g., a tumor) receives 100% of the prescribed dose, while the risk organs and the healthy tissue (non-target volume) receive absolute zero dose. As the beam typically intersects healthy tissue (and sometimes even the risk organ, e.g., if the tumor is surrounded by a risk organ) the aforesaid very strict constraints cannot be kept. That is, there is no treatment plan that can satisfy these strict constraints. Requiring the treatment planner to change the constraint settings and to try again is time consuming and against the idea of inverse planning. Conversely, if the constraints are too loose the patient doesn't receive the best possible treatment.

Thus, a need exists for an inverse planning system which can react effectively to the problem presented when not all desired constraints can be kept, while still allowing the system to generate a plan better than the desired one.

SUMMARY OF INVENTION

The present invention provides an inverse planning system (method and apparatus) which can react effectively to the problem presented when not all desired constraints can be kept, while still allowing the system to generate a plan better than the desired one. To this end and according to one embodiment of the invention, an inverse planning method for radiotherapy treatment of a target volume in a body comprises the steps of: using a computer to calculate the results (dose distribution) of multiple treatment solutions (proposed radiation beam arrangements); and simultaneously displaying the calculated results for at least two of the treatment solutions for comparison by a treatment planner to enable the treatment planner to select a desired one of the treatment solutions.

In a specific embodiment, the inverse planning method includes a non-constrained step of using a computer to obtain the multiple treatment solutions at two or more discrete calculations yielding X% of a prescribed dose throughout the target volume and (100-X)% protection of a non-target volume, where X has a position value between 0 and 100.

In a specific embodiment, the inverse planning method includes the step of identifying a first objective function indicating a desired distribution of dose in a plurality of volume elements within the target volume, the step of identifying a second objective function indicating a desired distribution of dose in a plurality of volume elements within the non-target volume, and the constrained step of using a computer to obtain the multiple treatment solutions at two or more discrete calculations weighting the first objective function at Y% and the second objective function at (100-Y)%.

In a specific embodiment, the multiple treatment solutions are obtained from calculations combining the non-constrained and constrained steps with variable weighting, thereby enabling consideration of the objective functions without eliminating the possibility to improve the treatment plan beyond the objective functions.

In a specific embodiment, the identifying steps include receiving the first and second objective functions from a treatment planner.

In a specific embodiment, the first and second objective functions are represented by dose volume histograms of desired dose distribution data for the target volume and the non-target volume, respectively.

In a specific embodiment, the calculations of the treatment solutions are set as default calculations or are defined by the treatment planner.

In a specific embodiment, the calculated results are displayed as 2D and/or 3D dose-distributions and resulting histograms.

In a specific embodiment, one or more parameters of the first and second objective functions are displayed.

In a specific embodiment, the inverse planning method includes the step of sequentially displaying different pairs of calculated results.

The invention also provides an apparatus for carrying out the method of the invention. More particularly, the invention provides an apparatus for inverse planning a radiotherapy treatment of a target volume in a body comprising a display and a logic device which calculates the results (dose distribution) of multiple treatment solutions (proposed radiation beam arrangements) and causes to be simultaneously displayed on the display the calculated results for at least two of the treatment solutions for comparison by a treatment planner to enable the treatment planner to select a desired one of the treatment solutions.

DETAILED DESCRIPTION

Figure 1:
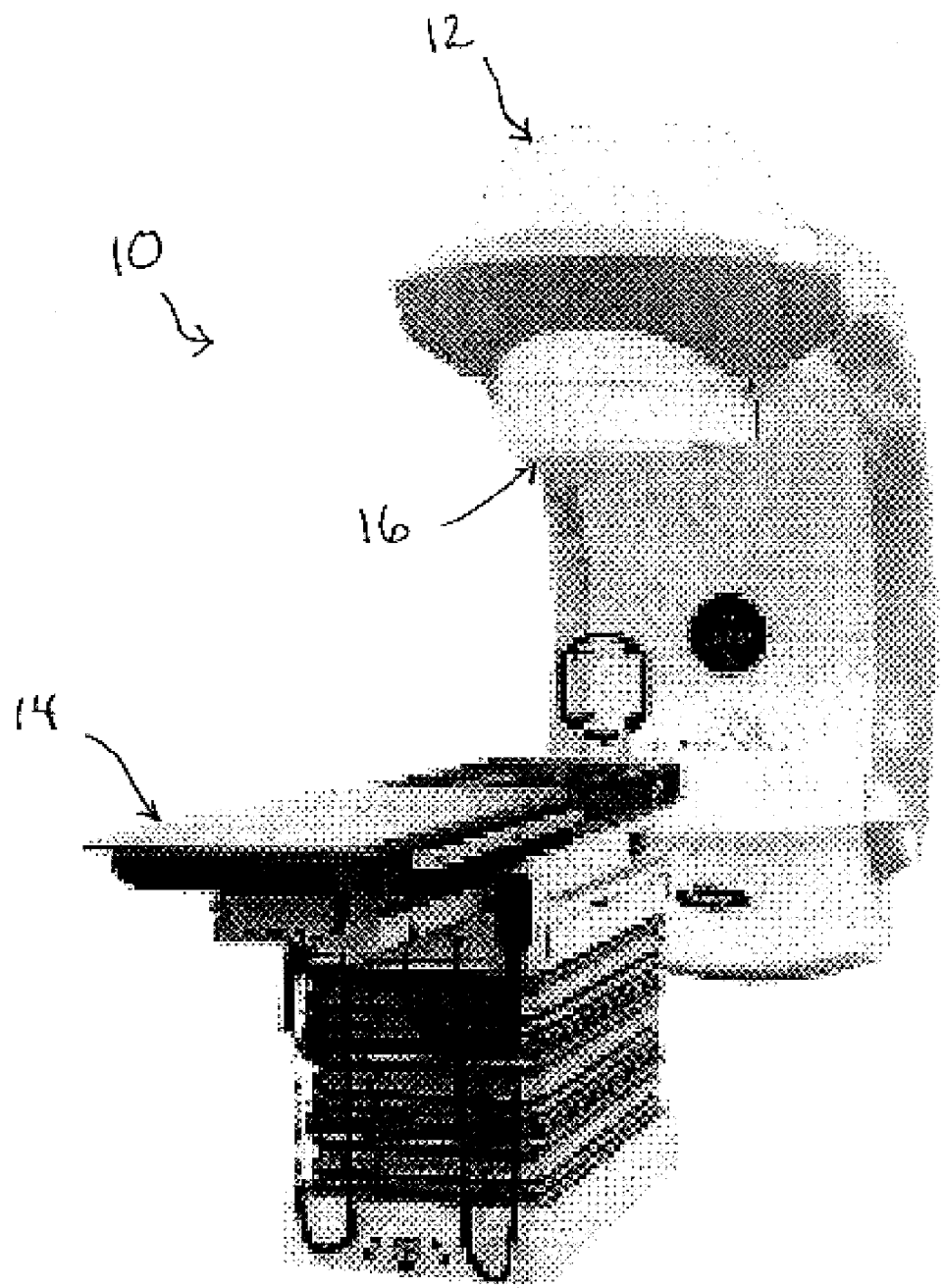
FIG. 1 is a perspective view of a conventional radiation therapy apparatus.

Referring now in detail to FIG. 1, an apparatus used to provide radiation therapy is designated generally by reference numeral 10. The apparatus 10 comprises a movable gantry 12 and a patient couch 14. The gantry 14 is mounted so as to allow revolution about a patient resting on the couch 14. The gantry includes a radiation source and collimator indicated at 16. The illustrated apparatus is the Novalis™ system available from BrainLAB AG, the assignee of the present invention. The Novalis™ system represents just one of may linear accelerator systems with which the present invention may be used to administer radiation in accordance with a prescribed treatment plan determined in accordance with the present invention. The invention is particularly useful with apparatus that can perform IMRT treatments (i.e., Intensity Modulated RadioTherapy treatments).

A typical radiation treatment process is as follows. First a series of three dimensional images are obtained, for example by conventional CT, MRI, SPECT or PET. The images are transferred to a treatment planning computer used by a treatment planner to prescribe an individual treatment plan—outlining the target volume which may be a tumor or other lesion. Once a desired treatment plan has been developed and after final verification, the apparatus is operated in accordance with the treatment plan to deliver the prescribed radiation dosage to the patient supported on the treatment coach.

Figure 2:
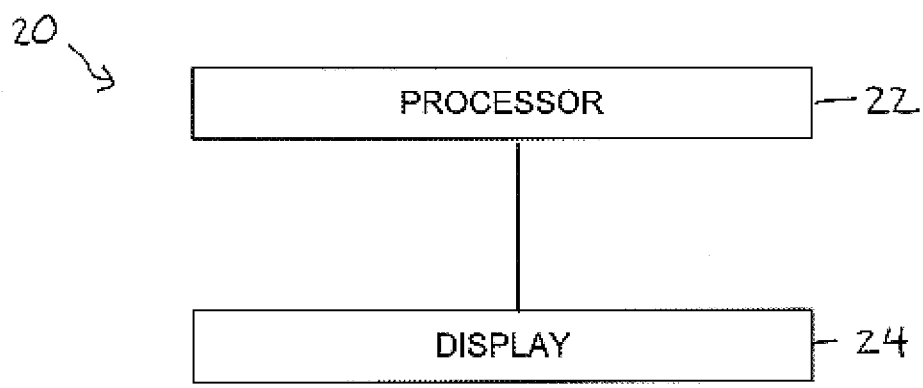
FIG. 2 is a diagrammatic illustration of a treatment planning system according to the invention.

The present invention principally relates to the treatment planning step and apparatus for carrying out treatment planning. An exemplary apparatus 20 is illustrated in FIG. 2 and generally comprises a logic device 22, e.g., a computer, and a display 24, e.g., a CRT. In accordance with the present invention, an inverse planning method for radiotherapy treatment of a target volume in a body generally comprises the steps of (a) using the logic device 22 to calculate the results (e.g., dose distribution) of multiple treatment solutions (e.g., proposed radiation beam arrangements); and (b) simultaneously displaying on the display 24 the calculated results for at least two of the treatment solutions for comparison by a treatment planner to enable the treatment planner to select a desired one of the treatment solutions. Basically, plural optimized plans are calculated with different constraint prioritizations for quick selection and elimination of the trial and error approach previously used. The inverse planning system (method and apparatus) of the invention can react effectively to the problem presented when not all desired constraints can be kept, while still allowing the system to generate a plan better than the desired one.

Figure 3:
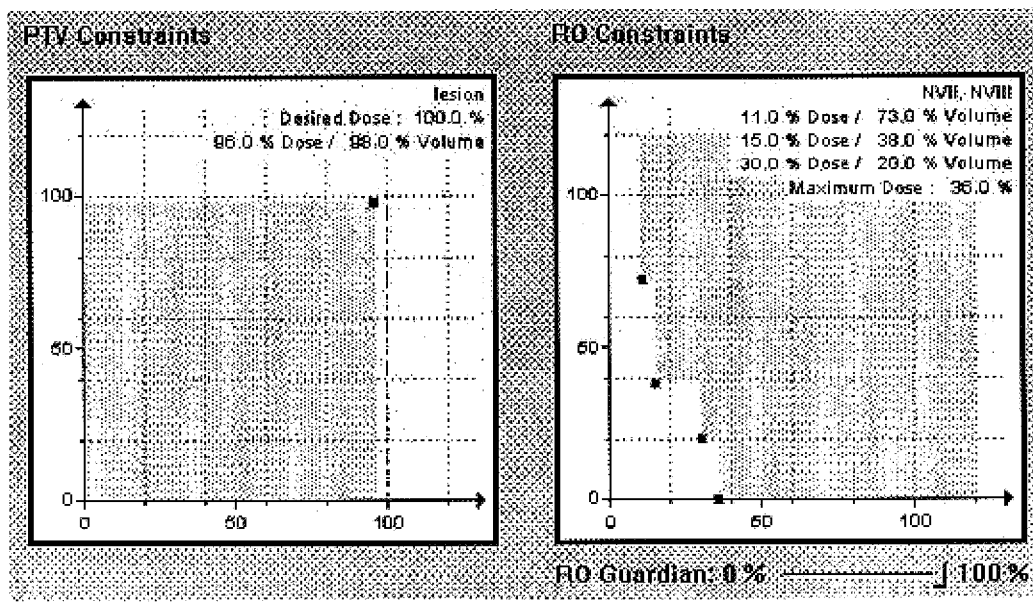
FIG. 3 are dose-volume histograms showing exemplary constraints for a tumor and a risk organ.

By way of a specific example of a method according to the invention, the treatment planner, e.g., a radiotherapist, simply specifies the ideal result by setting constraints in dose-volume histograms (DVH) for the target(s) and risk organs—an inverse planning process. The desired dose distribution may be specified by marking forbidden areas on a DVH sketch. The DVH is a standard radiotherapy treatment verification tool and is a well known tool in the art. In FIG. 3, the displayed example of a DVH indicates the forbidden areas (constraints) for the PTV (Planned Target Volume) and one RO (Risk Organ). The logic device will try to calculate a treatment plan, where the corresponding DVH graphs run outside the shaded areas. Although DVHs are preferably used, the "desired dose distribution" may be defined in different ways (e.g. drawing on the 2D CT slices), and/or by using other constraints, i.e., objective functions indicating a desired distribution of dose in a plurality of volume elements within the target volume and non-target volume.

The logic device may calculate, for example, four different plans, each with varying weight given to the risk organ constraints. These calculations may be performed using any suitable beam optimization technique and the logic device may be programmed accordingly using programming techniques well within those of a programmer having ordinary skill in the art. For example, calculation of an intensity distribution that best fulfills the specified requirements and constraints can be based on a very fast and accurate inverse planning algorithm developed by Jorge Llacer (Jorge Llacer, "Inverse radiation treatment planning using Dynamically Penalized Likelihood Method". In: Med. Phys. 24 (1997), pp. 1751–1764.).

Ideally the treatment planner would like to set the constraints in a way that the target volume (e.g., a tumor) receives 100% of the prescribed dose, while the risk organs and the healthy tissue (non-target volume) receive absolute zero dose. As the beam typically intersects healthy tissue (and sometimes even the risk organ, e.g., if the tumor is surrounded by a risk organ) the aforesaid very strict constraints cannot be kept. That is, there is no treatment plan that can satisfy these strict constraints. Requiring the treatment planner to change the constraint settings and to try again is time consuming and against the idea of inverse planning. Conversely, if the constraints are too loose the patient doesn't receive the best possible treatment.

The technique of the present invention solves the problem by suggesting "multiple treatment solutions". The multiple treatment solutions can be two or more discrete calculations within the following range: ideal target(s) dose coverage and 100% protection of risk-organ(s) and/or healthy tissue—ignoring the actual constraints. The multiple treatment solutions can be two or more discrete calculations within the following range: 100% keeping the constraints for the target(s) and 100% keeping the constraints for the risk-organ (s) and/or healthy tissue. The multiple treatment solutions can be two or more discrete calculations combining the above mentioned methods by mixing the first (non-constraint) and second (constraint) method with variable weighting. The combination method provides for consideration of the planner's constraints without eliminating the possibility to improve the treatment plan beyond these constraints.

The calculation position within the range and the number of calculation positions can be either system default or user defined.

Figure 4:
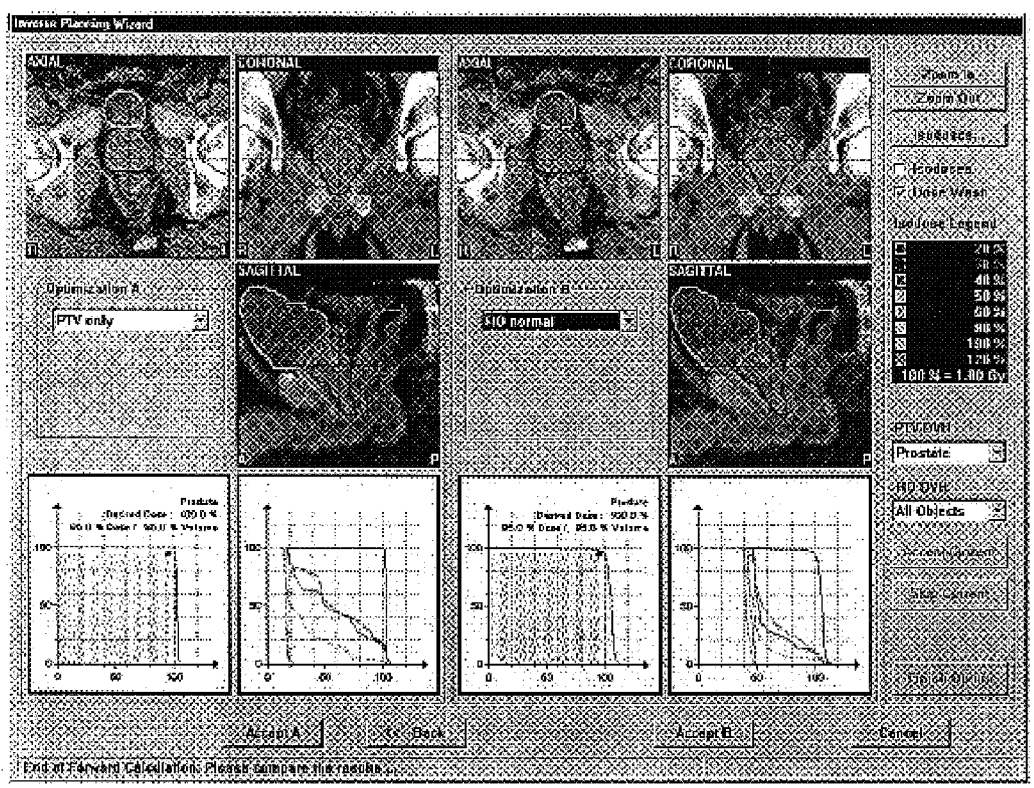
FIG. 4 is an exemplary display screen showing on the left side a plan only considering the target (PTV=Planned Target Volume) and on the right side a plan considering the risk organ with "normal" priority".

Two or more calculation results are displayed at the same time for comparative viewing by the treatment planner. This allows the planner to select the plan most appropriate for the patient's disease. The display may include (but is not restricted to) 2D and 3D dose-distributions and resulting histograms (including the constraint settings). The planner can easily switch between different plans. FIG. 4 is a display showing on the left side a plan only considering the target (=PTV=Planned Target Volume) and on the right side a plan considering the risk organ with "normal" priority.

The results of the four (or other desired number) plans may be simultaneously displayed or different combinations of the results may be simultaneously displayed for comparison and selection by the treatment planner. The treatment planner can choose the best plan for his particular case with a click of the mouse (used as an input device for the computer), instead of having to perform time-consuming recalculations. The result is a highly streamlined planning process. Consequently, the patient receives a conformal and homogeneous dose of radiation to the tumor while healthy tissue and adjacent critical organs are spared almost completely.

As used herein, "target volume" includes one or more targets and "non-target volume" includes one or more risk organs and/or healthy tissue.

What is claimed is:

1. An inverse planning method for radiotherapy treatment of a target volume in a body, said method comprising:

identifying a first objective function indicating a desired distribution of dose in a plurality of volume elements within the target volume;

identifying a second objective function indicating a desired distribution of dose in a plurality of volume elements within the non-target volume;

using a computer to calculate results of multiple treatment solutions at two or more discrete calculations with different risk organ weightings; and simultaneously displaying the calculated results for at least two of the treatment solutions for comparison by a treatment planner to enable the treatment planner to select a desired one of the treatment solutions; and wherein the multiple treatment solutions are obtained from calculations combining non-constrained and constrained steps with variable weighting, thereby enabling consideration of the objective functions without eliminating the possibility to improve the treatment plan beyond the objective functions.

2. An inverse planning method as set forth in claim 1, wherein the identifying steps include receiving the first and second objective functions from a treatment planner.

3. An inverse planning method as set forth in claim 1, wherein the first and second objective functions are represented by dose volume histograms of desired dose distribution data for the target volume and the non-target volume, respectively.

4. An inverse planning method as set forth in claim 1, wherein the calculations of the treatment solutions are set as default calculations or are defined by the treatment planner.

5. An inverse planning method as set forth in claim 1, wherein the calculated results are displayed as 2D and/or 3D dose-distributions and resulting histograms.

6. An inverse planning method as set forth in claim 5, wherein one or more parameters of the first and second objective functions are displayed.

7. An inverse planning method as set forth in claim 1, including the step of sequentially displaying different pairs of calculated results.

8. An apparatus for inverse planning a radiotherapy treatment of a target volume in a body comprising a display and a logic device which calculates the results of multiple treatment solutions based on a first objective function indicating a desired distribution of dose in a plurality of volume elements within the target volume and a second objective function indicating a desired distribution of dose in a plurality of volume elements within the non-target volume, and causes to be simultaneously displayed on the display the calculated results for at least two of the treatment solutions for comparison by a treatment planner to enable the treatment planner to select a desired one of the treatment solutions, wherein the logic device calculates results of multiple treatment solutions at two or more discrete calculations with different risk organ weightings, and the multiple treatment solutions are obtained from calculations combining non-constrained and constrained steps with variable weighting, thereby enabling consideration of the objective functions without eliminating the possibility to improve the treatment plan beyond the objective functions.

* * * * *